United States Patent
Shirai et al.

(10) Patent No.: US 11,526,989 B2
(45) Date of Patent: Dec. 13, 2022

(54) MEDICAL IMAGE PROCESSING APPARATUS, MEDICAL IMAGE ANALYSIS APPARATUS, AND STANDARD IMAGE GENERATION PROGRAM

(71) Applicant: Hitachi, Ltd., Tokyo (JP)

(72) Inventors: Toru Shirai, Tokyo (JP); Ryota Satoh, Tokyo (JP); Yasuo Kawata, Tokyo (JP); Tomoki Amemiya, Tokyo (JP); Yoshitaka Bito, Tokyo (JP); Hisaaki Ochi, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 375 days.

(21) Appl. No.: 16/890,042

(22) Filed: Jun. 2, 2020

(65) Prior Publication Data
US 2021/0166388 A1    Jun. 3, 2021

(30) Foreign Application Priority Data
Nov. 28, 2019   (JP) .............................. JP2019-215579

(51) Int. Cl.
*G06T 7/00* (2017.01)
*G16H 30/40* (2018.01)
(Continued)

(52) U.S. Cl.
CPC .......... *G06T 7/0014* (2013.01); *A61B 5/0042* (2013.01); *A61B 5/02042* (2013.01);
(Continued)

(58) Field of Classification Search
CPC ...... G06T 7/0014; G16H 50/70; G16H 50/20; G16H 30/40
See application file for complete search history.

(56) References Cited

U.S. PATENT DOCUMENTS 5,479,575 A  * 12/1995  Yoda .................... G06K 9/6272
                                                        706/31
9,042,616 B2    5/2015  Goto et al.

FOREIGN PATENT DOCUMENTS

JP            5601378 B2     10/2014

OTHER PUBLICATIONS

John Ashburner, "A fast diffeomorphic image registration algorithm", NeuroImage 38, 2007, pp. 95-113.

* cited by examiner

*Primary Examiner* — Edward Park
(74) *Attorney, Agent, or Firm* — Mattingly & Malur, PC

(57) ABSTRACT

In brain analysis, anatomical standardization is performed when analyzing a region of interest (ROI). There are individual differences in the shape and size of the brain and by converting the brain into a standard brain, these differences can be compared with each other and subjected to statistical analysis. When generating a standard brain analysis, a large number of pieces of image data are classified into a plurality of groups based on their anatomical features. An intermediate template that is an intermediate conversion image and a conversion map is calculated for each group, and the calculation of the intermediate template and the generation of the intermediate conversion image are repeated while gradually reducing the number of classifications, so that a final standard image is generated. Using the standard image and the intermediate template calculated during the generation of the standard image, spatial standardization of the measured image is performed.

15 Claims, 10 Drawing Sheets

(51) Int. Cl.
*G16H 50/70* (2018.01)
*G16H 50/20* (2018.01)
*A61B 5/00* (2006.01)
*A61B 5/02* (2006.01)
*A61B 5/03* (2006.01)
*G06F 16/51* (2019.01)
*G06F 16/55* (2019.01)

(52) U.S. Cl.
CPC ............ *A61B 5/031* (2013.01); *A61B 5/7264* (2013.01); *G06F 16/51* (2019.01); *G06F 16/55* (2019.01); *G16H 30/40* (2018.01); *G16H 50/20* (2018.01); *G16H 50/70* (2018.01); *G06T 2207/30016* (2013.01); *G06T 2207/30096* (2013.01)

MEDICAL IMAGE PROCESSING APPARATUS, MEDICAL IMAGE ANALYSIS APPARATUS, AND STANDARD IMAGE GENERATION PROGRAM

INCORPORATION BY REFERENCE

The present application claims priority from Japanese patent application JP-2019-215579 filed on Nov. 28, 2019, the content of which is hereby incorporated by reference into this application.

BACKGROUND OF THE INVENTION

Field of the Invention

The present invention relates to a medical image processing apparatus for analyzing a form, a function, and the like of an examination target using an image acquired by a medical imaging apparatus and in particular, to a technique for generating a standard image required for analysis.

Description of the Related Art

In the field of brain morphology analysis or brain function analysis, a technique has been developed in which changes in the volume of a predetermined part of an examination target are statistically analyzed (ROI analysis) using a large number of medical images to elucidate various brain diseases, individual differences, and the like. As a basic technique for analysis, image processing is indispensable.

In the brain analysis, anatomical standardization is performed when analyzing a region of interest (ROI). The anatomical standardization (also called spatial normalization or spatial standardization) is a process of converting an image to be analyzed, for example, a brain image, into an image of standard brain coordinates. The standard brain is a brain image having an average shape and size calculated from brain MRI images of a large number of subjects acquired in advance, and the position or the range of the ROI of each tissue of the brain, such as the hippocampus or the putamen, is designated. In general, there are individual differences in the shape and size of the brain. However, by converting the brain into a standard brain, these can be compared with each other and can be subjected to statistical analysis.

In the anatomical standardization, usually, a measured brain image (measured image) is segmented, for example, a map of white matter and gray matter is generated, a conversion map (displacement field matrix or transformation matrix) for converting the measured image into an image of standard brain coordinates based on the map is generated, and the conversion map is applied to the measured image to obtain an image converted into standard brain coordinates (converted image or standardized brain image). As conversion methods, methods such as affine transformation and non-rigid registration are generally known, and a DARTEL method has been proposed as a method with further improved accuracy (Ashburner J. "A fast deffeomorphic image registration algorithm", Neuroimage 2007; 38, 95-113).

In the DARTEL method, an intermediate template is generated from a plurality of images measured for each facility, a measured image to be analyzed is converted into the intermediate template (Dartel template), and then non-rigid registration is performed on a standard brain image stored in advance. This intermediate template is a so-called intermediate standard brain image standardized for each facility. By converting the measured image into an intermediate standard brain image and then performing registration instead of directly registering the measured image with respect to a standard brain image, it is possible to eliminate the influence, such as image variations at each facility. As a result, the accuracy of registration can be improved.

In addition, Japanese Patent No. 5601378 (paragraph 0075) discloses that, in ROI analysis of a brain image, spatial standardization of the brain image is performed using the DARTEL method. In addition, Japanese Patent No. 5601378 (paragraph 0075) discloses that a white matter or gray matter template (standard brain template) is generated for each age group or gender.

However, medical images have large individual differences. In particular, it is difficult to generate an accurate conversion map when there is a region where a shape change, such as a ventricular abnormality, is large in the measured brain image, and standard brain conversion often failed in the known method. In addition, when there is a white matter lesion or a brain tumor in the measured image, erroneous recognition occurs in the segmentation for generating the conversion map, and the standard brain conversion fails. The measured image for which conversion has failed is excluded from the analysis target.

SUMMARY OF THE INVENTION

An object of the invention is to provide a technique capable of appropriately performing anatomical standardization even when there is a region having a large shape change in a measured image or there is a lesion or the like that is likely to be recognized as other tissues, so that ROI analysis of a large number of subjects is possible.

According to a first aspect of the invention, when generating a standard brain, a large number of pieces of image data are classified into a plurality of groups based on their anatomical features or their similarities or attributes, an intermediate template that is an intermediate conversion image and conversion map is calculated for each group, and the calculation of the intermediate template and the generation of the intermediate conversion image are repeated while gradually reducing the number of classifications (groups), so that a final standard image is generated.

In addition, according to a second aspect of the invention, while following the same path as a classification stage (classification path) used when generating a standard image, processing for conversion (spatial standardization) from a measured image to a standard image for a specific target or processing for conversion from a standard image to a measured image is performed using an intermediate template calculated in each stage. In this specification, both conversion processes are collectively referred to as spatial standardization. In addition, for analyses using these, the former is referred to as standard brain analysis, and the latter is referred to as an individual brain analysis.

That is, a medical image processing apparatus of the invention is a medical image processing apparatus including a standard image generation unit that generates a standard image used for statistical analysis of a medical image. The standard image generation unit includes: an image classification unit that classifies a large number of medical images into a plurality of groups; a template calculation unit that calculates an intermediate template for each group; and a conversion processing unit that calculates a conversion image by performing conversion processing on an image forming each of the plurality of groups, the conversion processing being for conversion into an intermediate template for each group. The calculation of an intermediate template for each group by the template calculation unit and the calculation of a conversion image by the conversion processing unit are repeated for the conversion image calculated by the conversion processing unit while reducing the number of groups, and the template calculated by the template calculation unit for the group is set as the standard image when the number of groups becomes a minimum.

In addition, the medical image processing apparatus of the invention further includes: a storage unit that stores a classification path of the image classification unit and an intermediate template for each group calculated by the template calculation unit; and an analysis unit that statistically analyzes a predetermined medical image using a standardized image obtained by converting the predetermined medical image into the standard image or an inversely converted standard image obtained by inversely converting the standard image into the predetermined medical image. The conversion processing unit calculates the standardized image or the inversely converted standard image by repeatedly performing conversion processing using the intermediate template according to the classification path stored in the storage unit.

According to the invention, the calculation of the intermediate template is repeated while reducing the number of groups according to the classification, and a standard image is generated using the finally calculated template. In the case of performing spatial standardization of a predetermined medical image (measured image) using the standard image generated in this manner, even when the measured image includes an image with a large shape change region or a lesion image, it is possible to perform accurate spatial standardization by following the classification path used at the time of repetitive operation for generating a standard image. As a result, it is possible to improve the accuracy of medical image analysis using the standard image.

DETAILED DESCRIPTION OF THE INVENTION

Hereinafter, embodiments of a medical image analysis apparatus and a medical image processing apparatus of the invention will be described. Here, a case where a medical image is a brain image and a medical image analysis apparatus is a brain image analysis apparatus will be described as an example.

Figure 1:
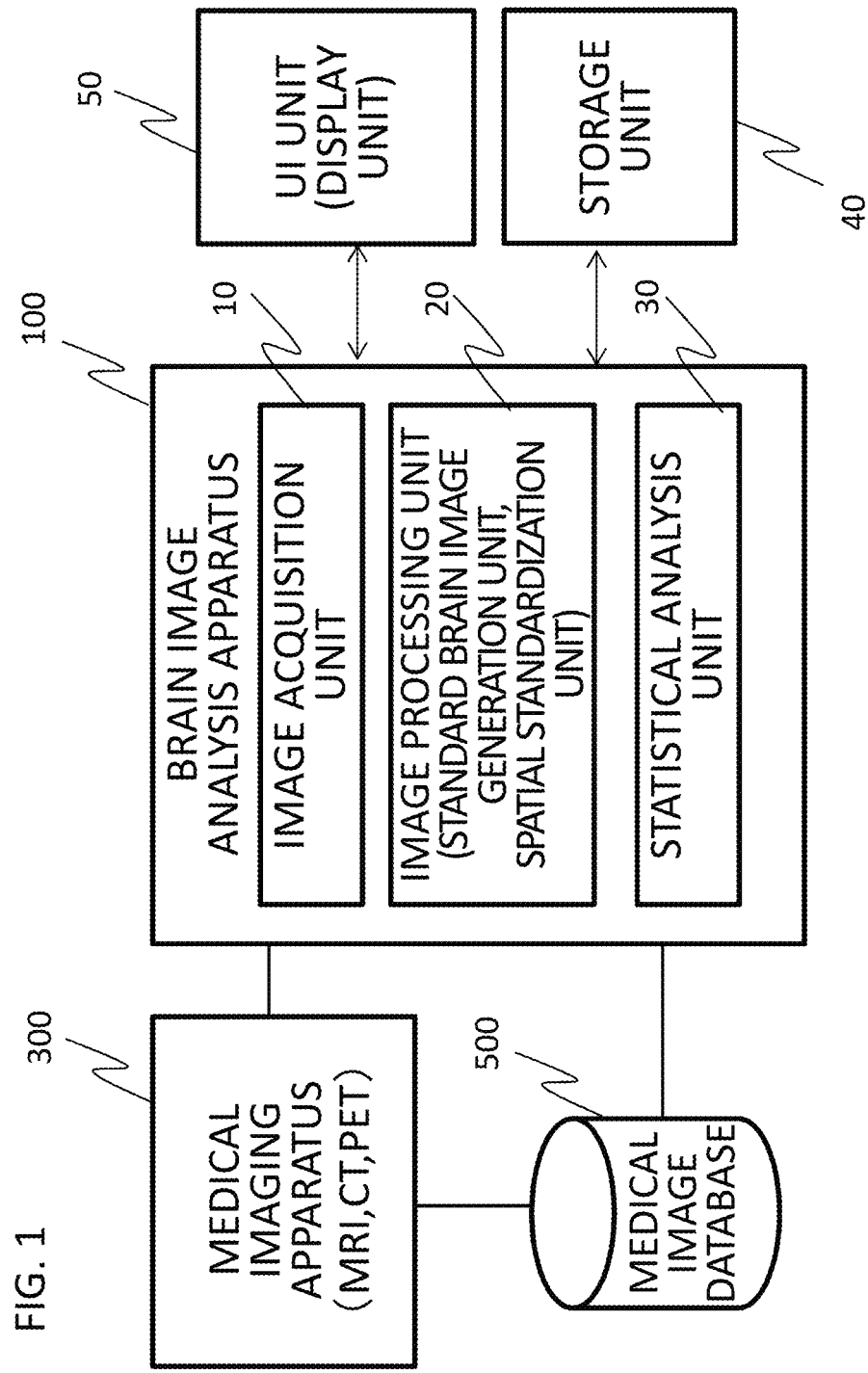
FIG. 1 is a diagram showing the overall configuration of a brain image analysis apparatus.

A brain image analysis apparatus 100 is an apparatus that analyzes brain images of a large number of subjects using the brain images. As shown in FIG. 1, the brain image analysis apparatus 100 includes: an image acquisition unit 10 that acquires a medical image, an image processing unit 20 that performs processing, such as image conversion, on the medical image; a statistical analysis unit 30 that performs statistical analysis of the form or function of the medical image; and a storage unit 40 that stores the acquired medical image, data being processed by each unit, and the like, and may further includes a UI unit 50 having an input device or a display device for presenting images or required information to the user.

As brain images handled by the brain image analysis apparatus 100, images acquired by medical imaging apparatuses such as an MRI image (for example, a T1-weighted image), a PET image, a CT image, and an ultrasonic image, and calculated images having quantitative values calculated from these as pixel values can be used. The brain image analysis apparatus 100 may be an apparatus attached to the medical imaging apparatuses, or may be an apparatus provided separately from the medical imaging apparatuses. In addition, some of the functions of the brain image analysis apparatus 100, for example, at least one of the image processing unit 20 and the statistical analysis unit 30 may be realized by an image processing apparatus (not shown) different from the brain image analysis apparatus 100.

When the brain image analysis apparatus 100 or the image processing apparatus realizing the above functions is an apparatus provided separately from the medical imaging apparatus, the brain image analysis apparatus 100 is connected to a medical imaging apparatus 300 or a medical image database 500, in which a large number of medical images are stored, through a network or the like. Therefore, the brain image analysis apparatus 100 acquires a desired image from the medical imaging apparatus 300 or the medical image database 500, and analyzes the acquired image.

The image processing unit 20 has a function as a standard brain image generation unit 20A that generates a standard brain image through image conversion using a transformation matrix (also referred to as a conversion map) using brain images of a large number of subjects, a function of generating a standardized image by registering an image measured for a specific subject (hereinafter, referred to as a measured image) with respect to a standard image using an intermediate template or a transformation matrix generated when the standard image is generated, or a function of generating an inversely converted standard brain image by performing image conversion on the generated standard brain image using an inverse matrix of the transformation matrix used for generating the standard brain image (function as a spatial standardization unit 20B).

Figure 2:
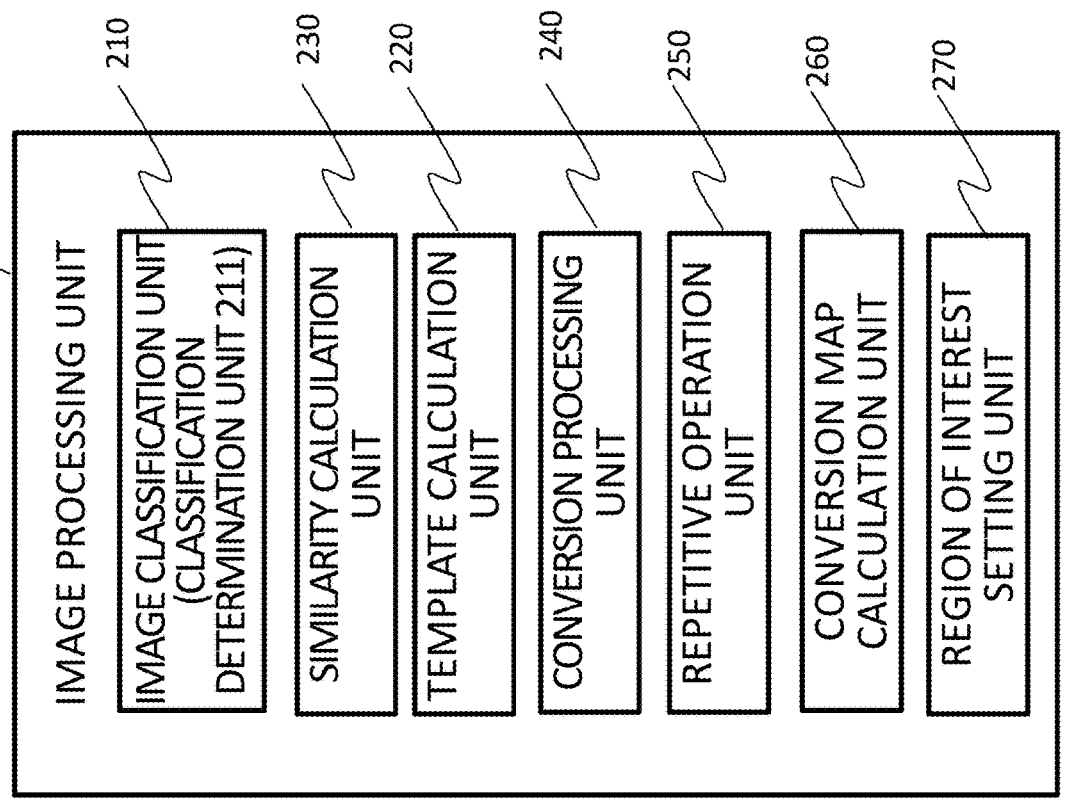
FIG. 2 is a functional block diagram of an image processing unit.

In order to achieve the function as the standard brain image generation unit 20A, as shown in FIG. 2, the image processing unit 20 includes: an image classification unit 210 that classifies brain images of a large number of subjects into a plurality of image groups based on morphological similarities (size of brain or brain tissue, presence or absence of disease, and the like) or subject attributes (gender, age, race, and the like); a template calculation unit 220 that calculates, from images forming a group, a template (intermediate template) that is a standard image of the images, for each of the plurality of image groups; and a conversion processing unit 240 that calculates a transformation matrix for registering each image with respect to the template and generates an intermediate conversion image by applying the transformation matrix to each image. In addition, in order to perform group classification or re-classification, a similarity calculation unit 230 that calculates the similarity inter-group may be provided separately from the image classification unit 210.

In addition, the image processing unit 20 includes a repetitive operation unit 250 that controls the operations of the above units to be repeatedly performed. The repetitive operation unit 250 reduces the number of groups to be classified for the conversion image (intermediate conversion image) generated by the conversion processing unit 240 for each group, and repeats template calculation, transformation matrix calculation, and conversion processing by the template calculation unit 220 for each reduced group until the number of groups becomes one. When the number of groups finally becomes the minimum, that is, when the number of groups becomes one, the image processing unit 20 (standard image generation unit 20A) sets the template calculated for the group as a standard image (standard brain image) template. In such a repetitive operation, the intermediate template calculated for each classification group and for each repetition is stored in, for example, the storage unit 40 together with information on the group and the number of repetitions.

In addition to the template calculation unit 220 and the conversion processing unit 240, in order to achieve the function as the spatial standardization unit 20B, the image processing unit 20 includes a classification determination unit 211 that determines to which group a measured brain image belongs according to the classification by the image classification unit 210 and determines each stage (classification path) of the classification that has reached a standard brain image through a plurality of conversion images with the image of the group as a starting point at the time of generating a standard brain image. In addition, the processing performed by the classification determination unit 211 is basically the same as the processing performed by the image classification unit 210. Therefore, the image classification unit 210 can also function as the classification determination unit 211.

The image processing unit 20 repeats the conversion processing using the transformation matrix, which is calculated in each stage of the classification, on the measured image according to the determination result of the classification determination unit 211, and performs registration on the standard image. For the registration, any of a method of performing anatomical standardization (conversion into the coordinates of the standard brain) on the measured brain image and performing analysis (first method) and a method of converting the standard brain image into the coordinates of the measured brain image (inverse conversion into the individual brain) and performing analysis (second method) may be adopted. When performing registration by the second method, the image processing unit 20 calculates a transformation matrix (inverse conversion map) in a direction opposite to that of the first method, and applies this to the intermediate template. For this reason, the image processing unit 20 includes a conversion map calculation unit 260 that calculates a conversion map and an inverse conversion map.

In addition, in order to perform an ROI analysis in the statistical analysis unit 30 described later, the image processing unit 20 includes a region of interest setting unit 270 that sets an ROI in a medical image. The region of interest setting unit 270 extracts the features of a region using the pixel values of each region of the medical image, and automatically sets the ROI. In addition, some of the functions of the image processing unit 20 shown in FIG. 3 can be omitted depending on the processing performed by the image processing unit.

The statistical analysis unit 30 analyzes a brain image measured for a predetermined subject (hereinafter, referred to as a measured brain image) by applying a brain atlas showing a region of each part of the brain set for the final template generated by the image processing unit 20. The analysis in the statistical analysis unit 30 is the same as a known brain analysis method, and can be realized by known software, such as SSP (Statistical Parametric Mapping) or 3DSSP (3-Dimensional Stereotactic Surface Projection). Therefore, although the methods are not described in detail in this specification, for example, a t-test or a correlation analysis is performed on the volume of a specific ROI (white matter, gray matter, or other brain tissues) using these methods, and a deviation from the average value of the volume, left and right difference, and presence or absence of a lesion are analyzed. The statistical analysis unit 30 may generate an image in which a value (such as a z value) obtained by the analysis is a pixel value.

The standard brain image generated by the image processing unit 20 (standard brain image generation unit 20A) or the statistical analysis unit 30, the analysis result of the statistical analysis unit 30, and the like may be displayed on a display device. For example, the UI unit 50 may present the user with the classification path obtained by the image classification unit 210, the intermediate template of each group calculated by the template calculation unit 220, and the like. Therefore, the user can check the repetitive operation or the transition of the template calculated at that time. In addition, regarding the processing of the standard brain generation unit 20 and the statistical analysis unit 30 or the display on the display device, it is also possible to receive conditions, instructions, or the like from the user through the UI unit 50.

The functions of the image processing unit 20 and the statistical analysis unit 30 can be realized as software by a general-purpose computer including a CPU or a GPU and a memory (storage unit 40). However, some operations and the like may be realized by a PCD (programmable logic device), such as an ASIC or an FPGA.

Figure 3:
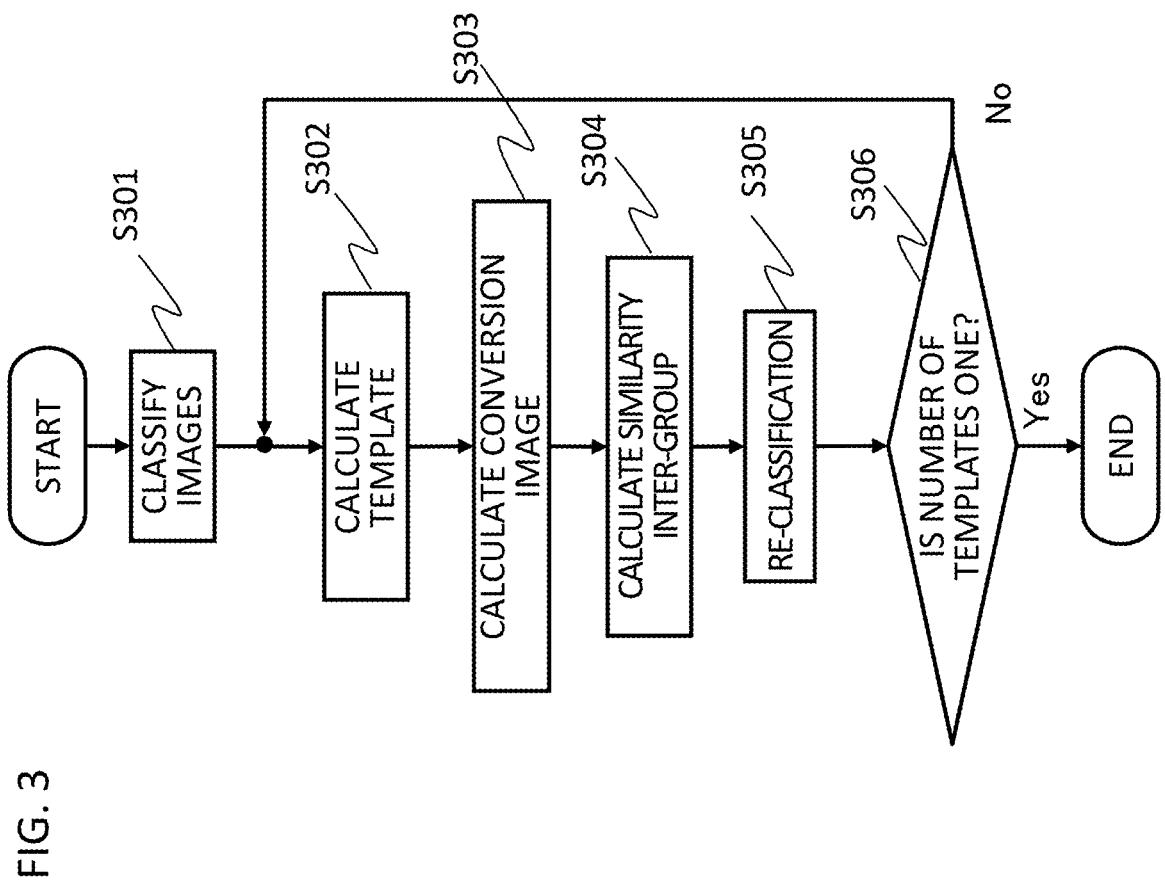
FIG. 3 is a diagram showing a process of the brain image analysis apparatus.

Next, processing of the image processing unit 20 in the brain image analysis apparatus 100 will be described. The processing of the image processing unit 20 includes a step of generating a standard brain image and a step of performing registration between a predetermined image and the standard brain image. As shown in FIG. 3, the procedure for generating a standard brain image includes: a step S301 of classifying a large number of images into a plurality of groups (classes); a step S302 of calculating an intermediate template for each group; a step S303 of calculating a conversion image by performing processing for converting images forming each of the plurality of groups into an intermediate template for each group; steps S304 and S305 of reclassify the groups to reduce the number of groups; and a step S306 of repeating the calculation of the intermediate template and the calculation of the conversion image for each group for the conversion image of a new group. When the number of groups becomes the minimum, that is, when the number of templates calculated in step S302 becomes one, the template is set as a template of a standard image.

For the procedure for standardizing a predetermined image, it is possible to adopt one of two methods, that is, a method of registering a predetermined image with respect to a standard brain image (first method) and a method of registering a standard brain image with respect to a predetermined image (individual brain) (second method). In any of the methods, in the step of generating a standard brain image, processing is repeatedly performed so that the same path as the classification path determined according to the classification group is used at the time of standardization, thereby performing standardization. At this time, when generating a standard brain image, the conversion processing is repeated using the intermediate template calculated in each stage and the transformation matrix obtained during the conversion processing. In addition, although not shown, smoothing processing that is a general technique in brain image analysis may be performed after the standardization. Therefore, since positional errors and individual differences can be reduced, the SN ratio is improved.

Thereafter, when registration is performed by the first method, the statistical analysis unit 30 performs statistical analysis for each ROI using a standardized image obtained by converting a predetermined medical image into a standard image. In addition, when registration is performed by the second method, the statistical analysis unit 30 performs statistical analysis on a predetermined medical image using an inversely converted standard image obtained by inversely converting a standard brain image into a predetermined medical image.

According to the brain image analysis apparatus 100 of the present embodiment, classification is repeated while reducing the number of groups to be classified, an intermediate template is calculated for each of the classified groups, and one template is finally obtained. Even when a measured image is registered with respect to the final template to perform spatial standardization, accurate spatial standardization can be performed by performing processing for conversion into the same intermediate template in each of the repetitive stages. As a result, the accuracy of the statistical analysis can be improved.

Hereinafter, an embodiment of the processing of the image processing unit 20 will be described. In the following embodiment, the configuration of an apparatus is the same as the configuration of the above-described embodiment unless otherwise specified.

First Embodiment

Figure 4:
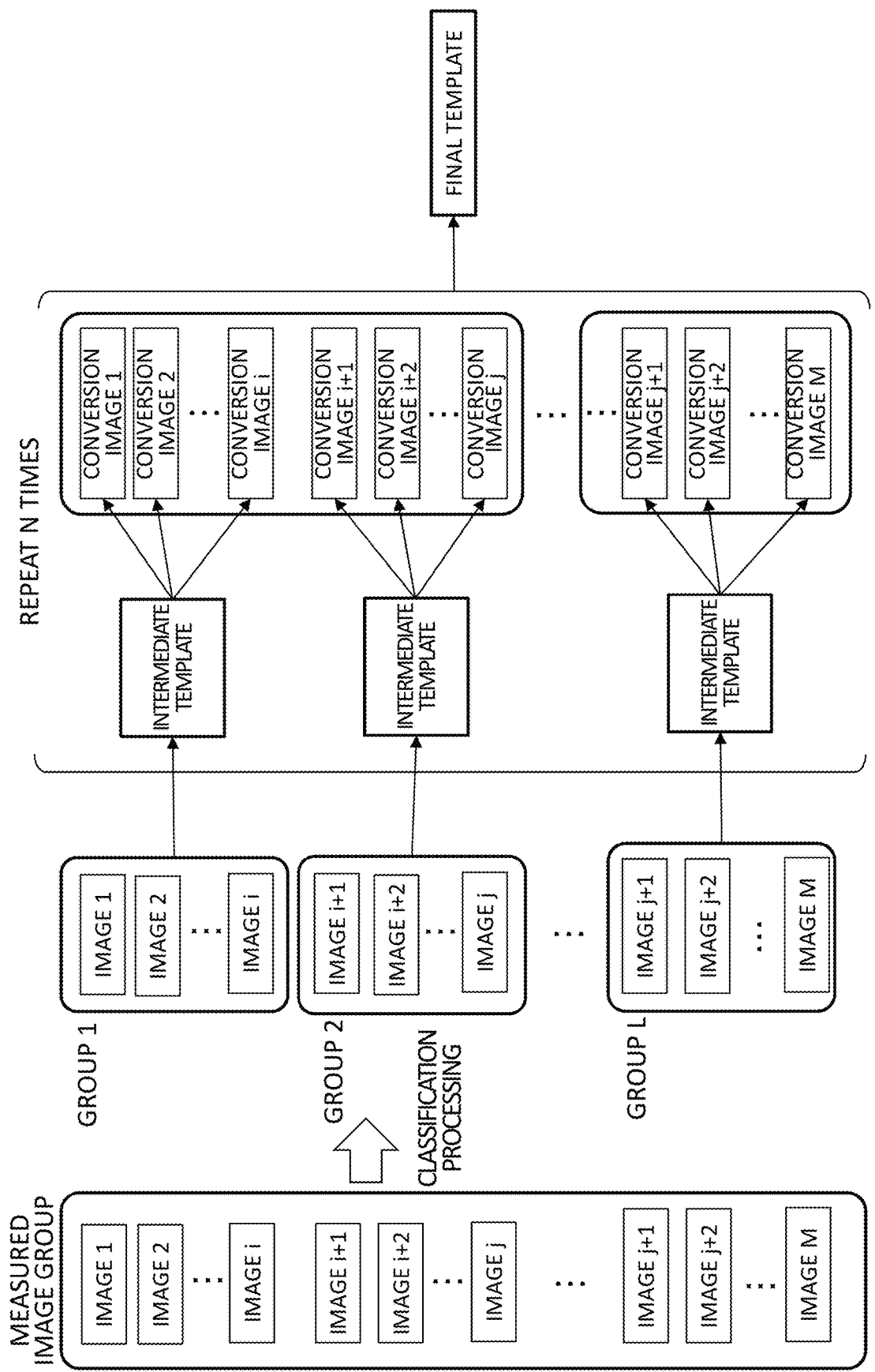
FIG. 4 is a diagram schematically showing a process of a standard image generation unit according to a first embodiment.
Figure 5:
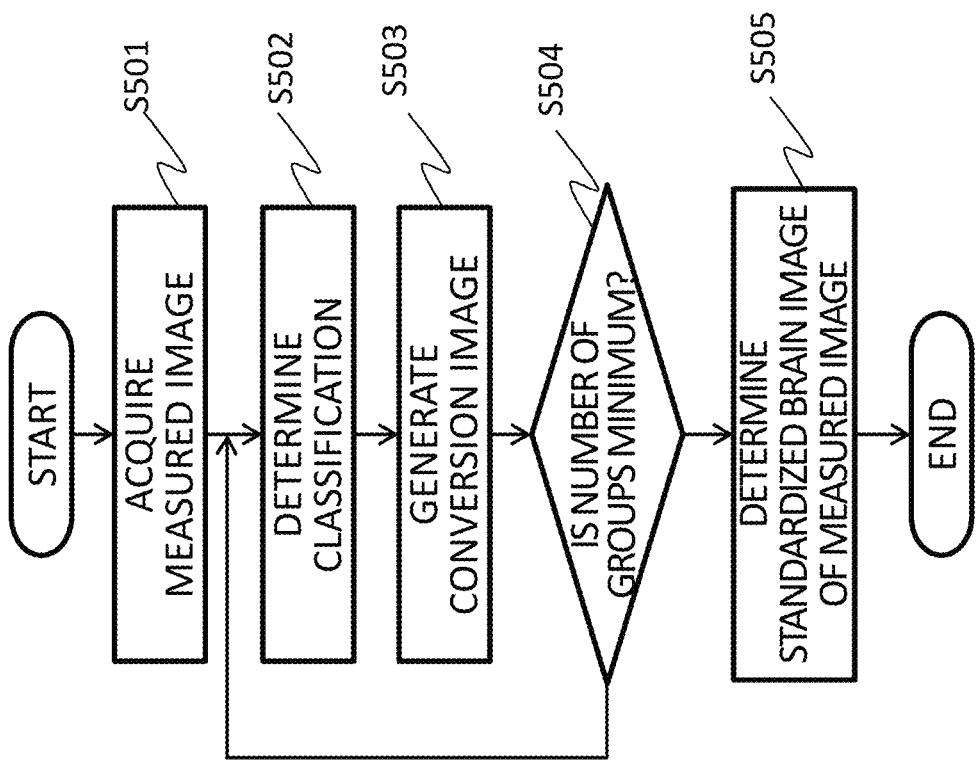
FIG. 5 is a diagram showing a process flow of a spatial standardization unit according to the first embodiment.
Figure 6:
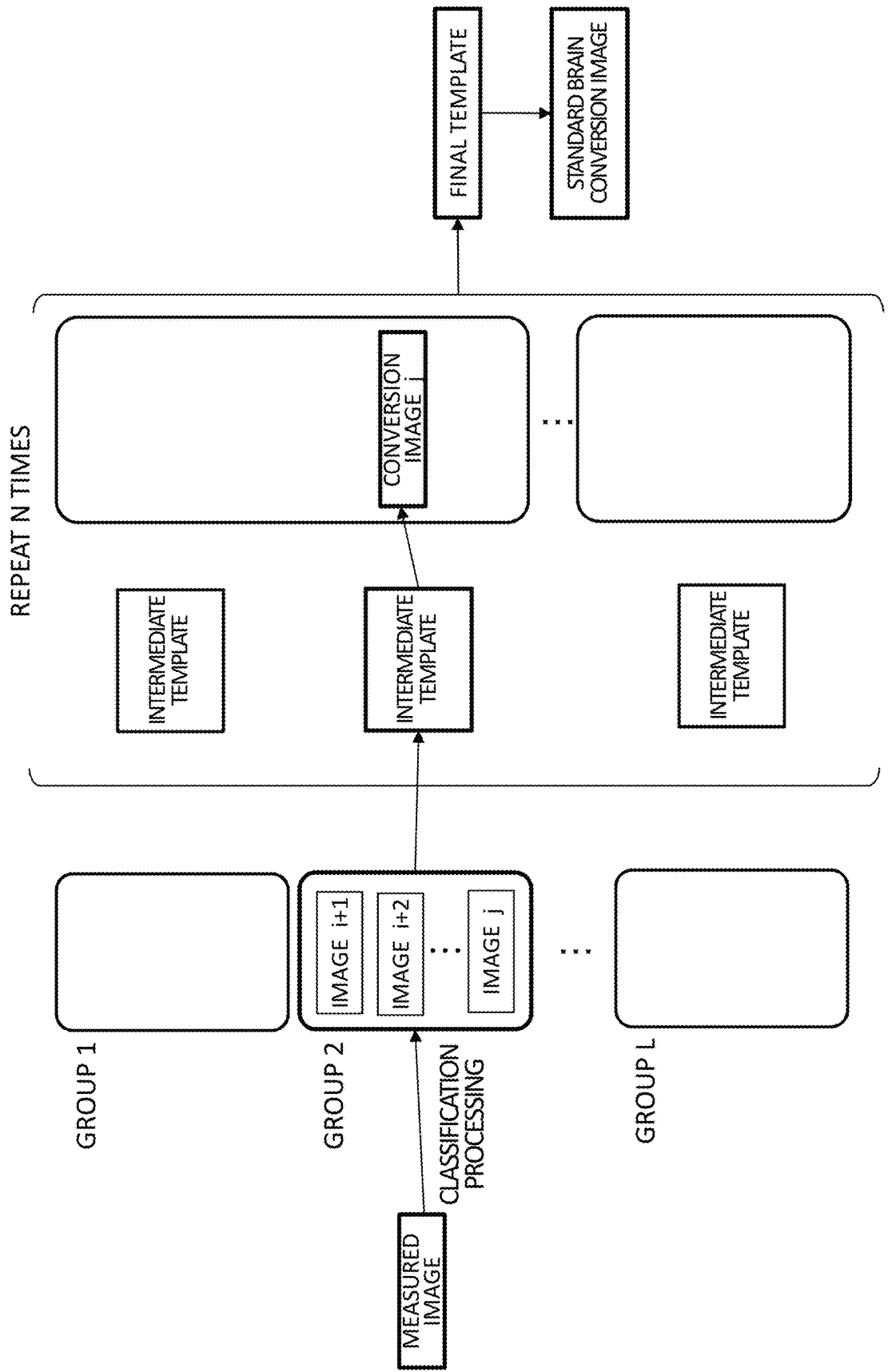
FIG. 6 is a diagram schematically showing a process of the spatial standardization unit according to the first embodiment.

In the present embodiment, the first method is used in spatial standardization. Hereinafter, the processing of the image processing unit 20 in the present embodiment will be described with reference to FIGS. 3 and 4 to 6. FIG. 4 shows the processing of the standard image generation unit 20A, and FIGS. 5 and 6 show the processing of the spatial standardization unit 20B.

First, the image acquisition unit 10 acquires brain images of a large number of subjects from the medical imaging apparatus 300 or the medical image database 500. The brain images of a large number of subjects are, for example, T1-weighted images acquired by an MRI apparatus. It is preferable that these images are subjected to correction of a change in signal strength (STC: Slice Timing Correction) caused by a shift in imaging timing of a cross-sectional position in a 3D image, body motion artifact correction, and the like in advance.

The image classification unit 210 classifies a large number of brain images according to their attributes (S301). The classification method may be based on anatomical features, such as the size of the brain or ventricle, and variable amounts (parameters), such as age and gender, or may be based on an algorithm, such as a self-organizing map (SOM) or a decision tree. Classification based on anatomical features may include the presence or absence of a lesion. For example, it is possible to use a method of determining a ventricular abnormality (normal pressure hydrocephalus) from a deviation from a standard value of the ventricle size using white matter images and gray matter images obtained by segmenting the measured image and a method of determining a white matter lesion or a brain tumor from white matter pixel values. In addition, it is also possible to detect local hemorrhage of the brain from the features of the image using an AI algorithm or the like.

The number of groups generated by the classification is not particularly limited as long as the number of groups is 2 or more. When the above-described algorithm is used, the number of groups can be set in advance. In the example shown in FIG. 4, a state in which M images are classified into L groups is shown.

Then, the template calculation unit 220 generates an intermediate template for each image group using the images included in the group (S302). The intermediate template is an image having the most standard shape among the images included in the group. For example, a conversion parameter (transformation matrix) for superimposing the contours of two images in the group is calculated on a brute force basis, and an image having a conversion parameter closest to the average value of the conversion parameters is set as a standard image (intermediate template) of the group. A known method such as an affine transformation, a non-rigid transformation, and a non-linear transformation such as the DARTEL method can be adopted for the conversion processing for superimposing images.

In the case of the former method, in order to optimize the initial conditions of the convergence calculation and perform appropriate conversion, restriction conditions are introduced using a probability distribution reflecting the position of a brain part that is easily specified. Specifically, prior to processing for obtaining the transformation matrix, segmentation processing on the brain image is performed to divide the brain image into regions such as white matter and gray matter, and these segmentation images are generated. For the segmentation images, a conversion parameter between the images is obtained.

The intermediate template (intermediate standard image) obtained in this manner is stored in the storage unit 40.

Then, the conversion processing unit 240 generates a first conversion image for each image in the image group using the intermediate template generated in step S302 (S303). This processing is processing for registering the measured image with respect to the intermediate template. As in the case of obtaining the intermediate template, a known spatial standardization method such as an affine transformation, a non-rigid transformation, or a nonlinear transformation such as the DARTEL method can be adopted. Also in this case, a segmentation image can be used as a measured image. By using the segmentation image, conversion is performed with constraints for each tissue probability map. Therefore, the calculation does not diverge and the calculation efficiency can be improved. The transformation matrix is obtained by mapping the value of the conversion parameter for each position, and is calculated for each measured image during the registration processing. The transformation matrix (first transformation matrix) calculated in step S303 is stored in the storage unit 40 together with the intermediate template.

The shape of the obtained conversion image approximately matches that of the intermediate template, but tissue information represented by detail shape differences or pixel values is stored as it is. By this processing, the same number (M) of conversion images as the number of original images is obtained.

The repetitive operation unit 250 repeats the classification by the image classification unit 210, the calculation of the intermediate template by the template calculation unit 220, and the conversion processing of the conversion processing unit 240 for the conversion image obtained as described above (S304). Here, the classification by the image classification unit 210 is performed such that the number of groups is smaller than L in the next classification, where L is the first number of groups. In a case where a clustering algorithm is used, the number of groups is set such that the number of groups gradually decreases in the algorithm. In this case, the similarity calculation unit 230 calculates the similarity inter-group in advance, and unites groups with high similarity to gradually reduce the number of groups. The similarity can be calculated by a known method, such as residual sum of squares (SSD), normalized cross-correlation (NCC), and mutual information (MI). In addition, instead of calculating the similarity each time after classification, it is also possible to determine the rules of re-classification in advance.

In addition, when classification is performed based on a variable amount such as a parameter, the number or type of parameters used for classification may be changed. For example, classification is performed from the bottom to the top of the tree structure, such that classification is performed by combining three parameters (gender, age, and brain size) in the first classification (S301) and large classification is performed using one or two of the parameters in the second classification. In addition, when the similarity calculation and the re-classification are performed for each repetition, the classification method may be different between the first classification and the subsequent classification. For example, the first classification may be performed using parameters, and the second and the subsequent classifications may be performed using a clustering algorithm.

In the repetitive operation, an intermediate template (second intermediate template) is generated for each of new image groups (groups smaller than L) having conversion images as elements of each group in the same manner as in step S302, and each image (first conversion image) included in the group is converted into the intermediate template to generate a conversion image (second conversion image). That is, in the second processing, the same number of intermediate templates as the number of new image groups are generated, and the same number of conversion images as the number of original measured brain images are generated. The repetitive operation unit 250 repeats the re-classification for reducing the number of groups, the calculation of the intermediate template, and the conversion image generation processing until the number of groups becomes one. As a result, when the number of repetitions becomes N, one template is obtained for one group (an image group including M N-th conversion images). This template is a final template (standard image).

In addition, this final template may be converted into a standard template, such as Talairach coordinates or MINI standard coordinates. The standard image generation unit 20A sets a region (ROI) of each tissue by applying a brain map (atlas) to the final template.

The above-described steps are the processing of the standard image generation unit 20A.

The spatial standardization unit 20B performs spatial standardization on a measured brain image acquired for a predetermined subject, using the standard brain image generated by the standard brain image generation unit 20A and the intermediate template obtained during the repetitive operation. First, as shown in FIG. 5, the image acquisition unit 10 acquires a measured brain image as a target (S501). The image classification unit 210 or the classification determination unit 211 determines to which group the acquired measured brain image belongs according to the classification method at the time of generating the standard image (S502). That is, classification is performed according to the anatomical features or attributes (parameters) of the measured brain image, and a group to which the measured brain image belongs is determined. In the example shown in FIG. 6, the measured brain image is classified into group 2 among L groups.

When the group to which the measured brain image belongs is determined, the conversion processing unit 240 converts the measured brain image stored in the storage unit 40 into an intermediate template (first time) of the group to generate a first conversion image (S503). For the first conversion image, a group of second re-classification by the image classification unit 210 at the time of generating the standard brain is determined. The intermediate template of the determined group, that is, the second intermediate template is read from the storage unit 40 and applied to the first conversion image to generate a second conversion image. Similarly, classification (group determination) and conversion processing using the intermediate template are repeated until the group of the classification becomes the minimum value, thereby acquiring a conversion image converted into the final template (N-th template) (S505). The conversion image is an image (standard brain conversion image) converted into the coordinates of the standard brain image finally generated in the standard brain generation step (FIG. 3), that is, an image whose shape approximately matches that of the measured brain image and for which information of the original measured brain image is stored as it is as tissue information represented by pixel values. In addition, since a detail shape difference from the standard brain image remains, smoothing processing, pixel value modulation processing, and the like may be performed as necessary in order to eliminate the difference.

The statistical analysis unit 30 compares the segmented image of the final conversion image with a standard brain image, and calculates statistical amounts, such as an average value, a median value, and a standard deviation of pixel values in a tissue (ROI), for example, white matter or gray matter. From these statistical amounts, it is possible to obtain useful information for diagnosing a brain disease, such as a deviation of the ROI volume of the subject.

According to the present embodiment, based on the classification result of the measured image, in the standard brain image generation, spatial standardization is performed by following the same path as the repeated path from the image of the group to which the measured image belongs to the standard brain image. Therefore, accurate spatial standardization can be performed without being affected by differences inter-group. As a result, the accuracy of the statistical analysis can be improved.

Second Embodiment

Figure 7:
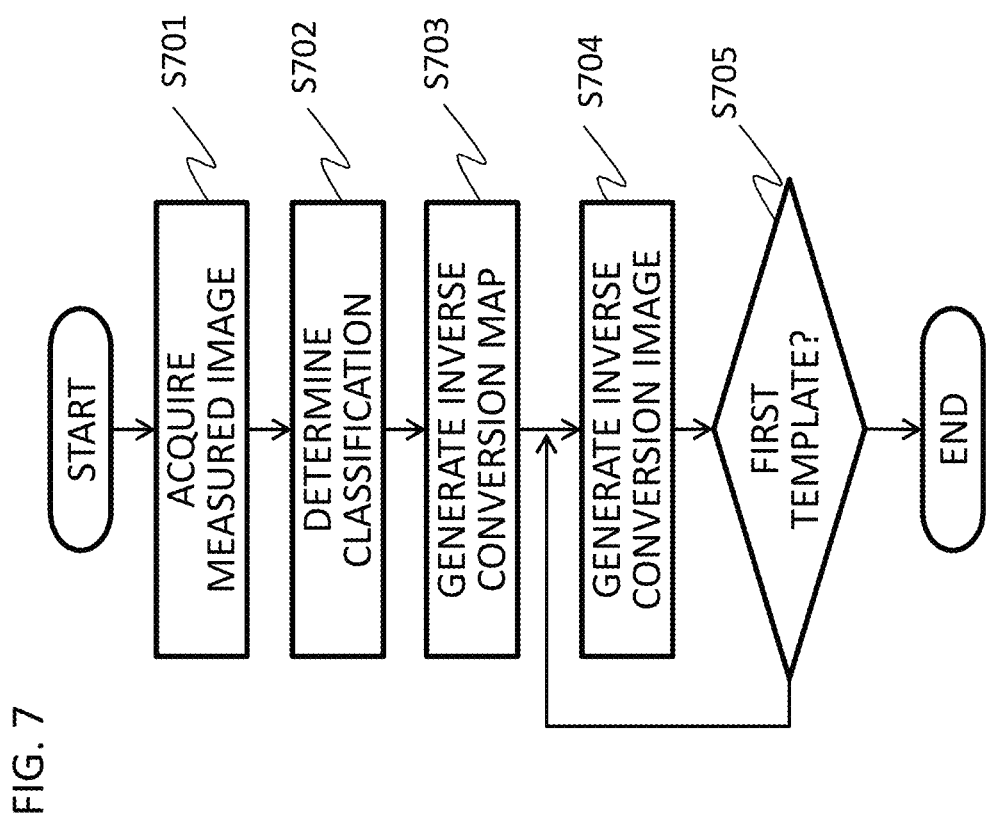
FIG. 7 is a diagram showing a process flow of a spatial standardization unit according to a second embodiment.

In the present embodiment, a second method (inverse conversion into the individual brain) is used for spatial standardization. Since the standard brain image generation step is the same as the procedure in the first embodiment shown in FIGS. 3 and 4, the description thereof is omitted, and the procedure of the spatial standardization unit 20B will be described with reference to FIG. 7.

When the image acquisition unit 10 acquires a measured brain image as a target (S701), the image classification unit 210 (classification determination unit 211) in the spatial standardization unit 20B determines to which group the acquired measured brain image belongs according to the classification method at the time of generating the standard image (S702), and determines a re-classification group to which the determined group belongs in the repeated processing up to the generation of the standard image. When the number of repetitions is N, 1 to N groups are determined. The number of groups in the last (N-th) repetition of the standard image generation is one.

When a group to which the measured brain image belongs and its path are determined, the conversion map calculation unit 260 calculates a conversion map between intermediate templates of adjacent groups in the repetition using the intermediate template of each determined group. That is, a conversion map from the first intermediate template to the second intermediate template, a conversion map from the second intermediate template to the third intermediate template, ..., a conversion map from the (N−1)-th intermediate template to the N-th intermediate template are calculated (S703). Then, the conversion map calculation unit 260 calculates inverse conversion maps of these conversion maps (S704). As a result, (N−1) inverse conversion maps are obtained. Using the inverse conversion maps, the conversion processing unit 240 sequentially performs an inverse conversion on the standard image (a final template or a template obtained by further converting the final template into a standard template) generated by the standard image generation unit 20A, thereby generating an inversely converted standard image (S705).

The inversely converted standard image obtained in this manner is an image whose shape approximately matches that of the measured image to be analyzed now, and information of the original standard brain image is stored as it is as tissue information represented by pixel values. As in the first embodiment, smoothing processing may be performed on the inversely converted standard image as necessary. Thereafter, by comparing the inversely converted standard image with the measured image, it is possible to calculate a statistical value, such as a difference in the volume of the measured image.

Also in the present embodiment, it is possible to improve the accuracy of spatial standardization as in the first embodiment. In addition, according to the present embodiment, since the error caused by the conversion is only the position and the shape of the ROI, there is an effect that the error of the signal value (average value or the like) at the time of ROI analysis is reduced.

Third Embodiment

In the first and second embodiments, classification is performed using medical images as they are, and standard images are generated or images are standardized. In the present embodiment, however, classification is performed after correcting measured images. For example, when classifying medical images, in the case of determining the presence or absence of an abnormal region using their anatomical features and the like, the abnormal region is corrected by an image correction unit. The images to be corrected are a large number of images for generating a standard image, but the correction may also be performed on a measured image to be subjected to spatial standardization.

Figure 8:
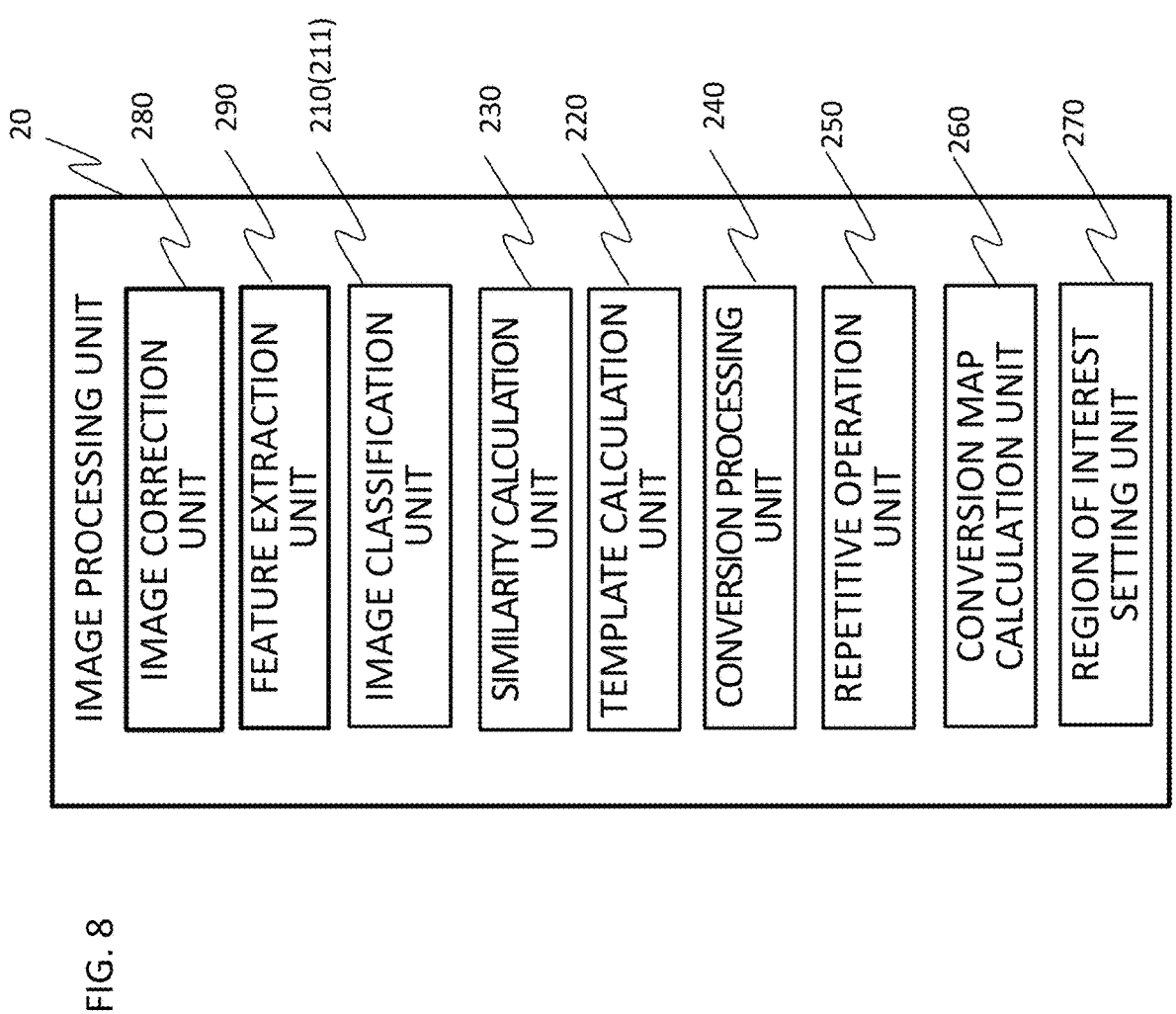
FIG. 8 is a block diagram showing the configuration of an image processing unit according to a third embodiment.
Figure 9:
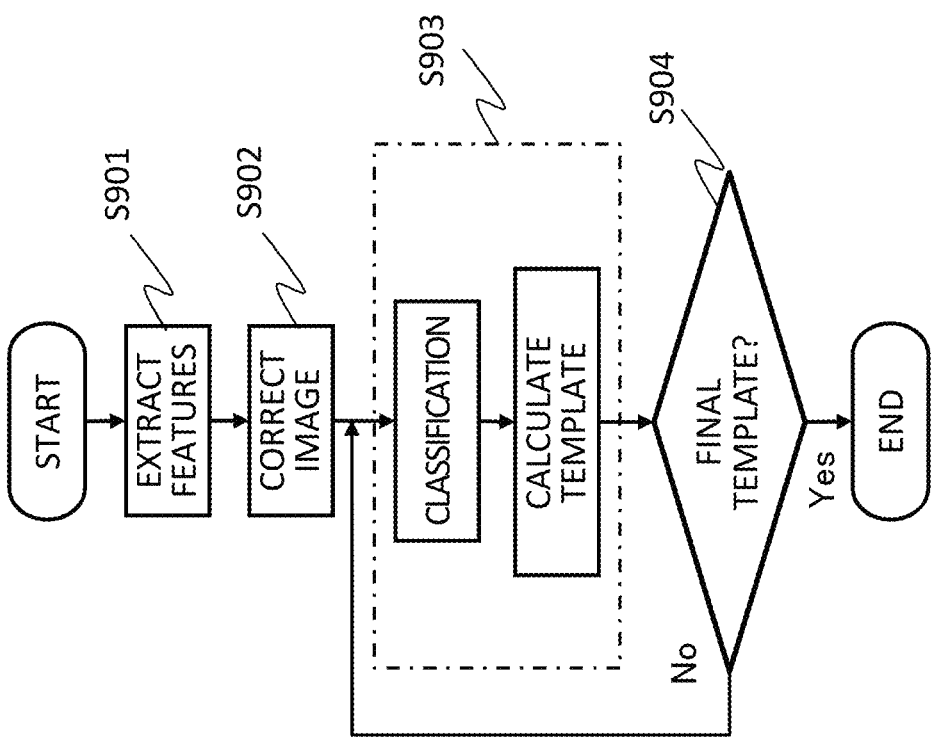
FIG. 9 is a diagram showing a process flow of the image processing unit according to the third embodiment.

As shown in FIG. 8, the image processing unit 20 according to the present embodiment includes an image correction unit 280 and a feature extraction unit 290 for extracting an abnormal part or a diseased part included in the image in addition to the configuration shown in FIG. 2. Other configurations are the same as those of the first embodiment or the second embodiment, and accordingly, the present embodiment will be described focusing on the differences. FIG. 9 shows a flow of the process according to the present embodiment.

When a medical image, for example, a brain image, is received by the image processing unit 20, the feature extraction unit 290 detects an abnormal part (S901). Similarly to the classification based on the anatomical features in the image classification unit 210 of the first embodiment, the feature extraction unit 290 may determine the presence or absence and the position of a ventricular abnormality, a white matter lesion, or a brain tumor from the deviation of the pixel value or the standard size value of segmentation images of the image, for example, a white matter image and a gray matter image, and extract an abnormal region, or may extract an abnormal region using an AI algorithm, such as deep learning. As the AI algorithm, an abnormality may be determined without teacher data, or an AI algorithm with teacher data learned to output a predetermined lesion or abnormality with respect to input data may be used.

The image correction unit 280 corrects the image by replacing the pixel values of the region specified as a lesion or an abnormality extracted by the feature extraction unit 290 with the pixel values of a normal tissue (S902). Since a region around the lesion or the abnormal region can be regarded as a normal tissue, the pixel values of the region specified as a lesion or an abnormality extracted by the feature extraction unit 290 are replaced with the pixel values of the surrounding region. Processing for eliminating other tissues for the pixels in the surrounding region used for replacement may be added.

After correcting the image in this manner, generating a standard image by performing repetitive operations according to the flow shown in FIG. 3 (S903 and S904) is the same as in the first and second embodiments. In FIG. 9, the procedure for generating a standardized image is shown. However, also for spatial standardization, spatial standardization is performed according to the flow shown in FIG. 5 or FIG. 7 after performing processings in steps S901 and S902 with respect to the acquired medical image.

That is, also in the spatial standardization of a measured image, the feature extraction unit 290 extracts an abnormal part from a measured image to be analyzed. When there is an abnormal part, correction using the pixel values of normal tissue pixels is performed. Then, the classification determination unit 211 (or the image classification unit 210) determines a group, and repeats processing for conversion into the intermediate template according to the classification (method of the first embodiment) or repeats inverse conversion processing on the standard brain image (method of the second embodiment), thereby performing spatial standardization.

In addition, in FIG. 9, a case is shown in which the classification is performed by the image classification unit 210 after correcting the abnormal region. However, the image classification unit 210 may first perform classification including the presence or absence of an abnormal part, and the image correction unit 280 may correct an image group classified as a group having an abnormal part. In this case, the medical image after the correction may be classified again by the image classification unit 210, and the process may proceed to the step of generating a standard image.

According to the present embodiment, even in a case where there are abnormalities or lesions for which the similarity for each classification cannot be accurately determined only by classification based on anatomical features, it is possible to perform standard image generation and spatial standardization using a standard image without excluding the data from the statistics and use the results for statistical analysis.

Figure 10:
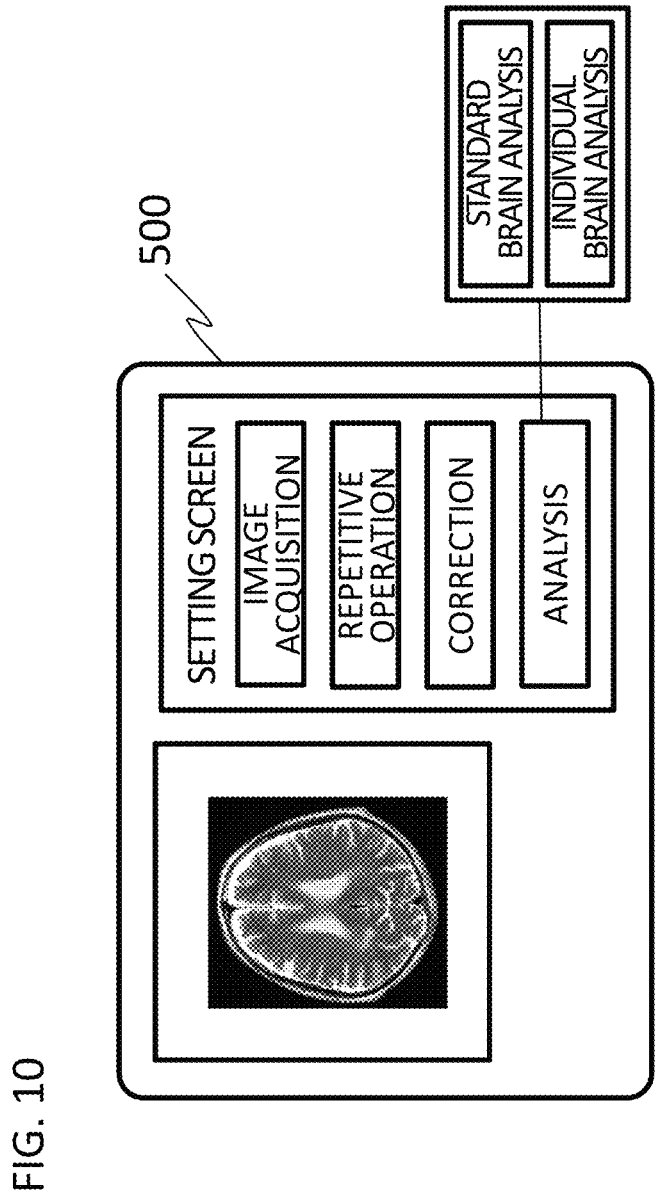
FIG. 10 is a diagram showing an example of a user interface screen.

While the first to third embodiments have been described above, which of these processes is to be performed may be set in the apparatus by default, or may be arbitrarily selectable by the user. FIG. 10 shows an example of a setting screen 50A of the UI unit 50 that receives user settings. Here, boxes indicating respective processes, such as image acquisition, repetitive operation, correction, and analysis, are displayed. When any of the boxes is selected, a pull-down menu or another screen is opened, so that the processing can be selected or the conditions can be set. For example, when the "analysis" box is selected, a box for selecting whether to perform the processing according to the first embodiment, that is, to perform the analysis using the standard brain, or to perform the processing according to the second embodiment, that is, to perform the analysis using the individual brain, is displayed to receive the user's selection. According to the user's selection, the image processing unit 20 performs either conversion into the standard brain after the generation of the standard brain or inverse conversion of the standard brain into the individual brain, and passes the result to the statistical analysis unit 30. In addition, by selecting the "correction" box, it is possible to select whether or not to perform correction. In addition, the user may designate the acquisition of the displayed image using the "image acquisition" box, or may set the number of repetitions of the "repetitive operation".

By providing such a UI screen, it is possible to improve the degree of freedom of processing.

What is claimed is:

1. A medical image processing apparatus, comprising:
   a processor coupled to a memory, the memory storing instructions that when executed by the processor, configure the processor to:
   generate a standard image used for statistical analysis of a medical image,
   classify a large number of medical images into a plurality of groups,
   calculate an intermediate template for each group, and
   calculate a conversion image by performing conversion processing on an image forming each of the plurality of groups, the conversion processing being for conversion into an intermediate template for each group, and
   wherein the calculation of an intermediate template for each group and the calculation of a conversion image are repeated for the conversion image while reducing the number of groups, and the intermediate template for the group is set as the standard image when the number of groups becomes a minimum.

2. The medical image processing apparatus according to claim 1,
   wherein the processor is configured to perform classification using at least one of anatomical features obtained from images and attributes of an examination target, such as age, gender, and physique.

3. The medical image processing apparatus according to claim 1,
   wherein the processor is configured to reduce the number of groups by combining groups having a high similarity for each repetition based on a classified similarity inter-group.

4. The medical image processing apparatus according to claim 1,
   wherein a classification structure is a tree structure, and
   wherein the processor is configured to reduce the number of groups by repeatedly performing processing from a bottom to a top of the tree structure.

5. The medical image processing apparatus according to claim 1,
   wherein the processor is configured to perform re classification on the conversion image at the time of repetitive operation.

6. The medical image processing apparatus according to claim 1, further comprising:
   a storage unit coupled to the processor that stores a classification path in the repetitive operation and an intermediate template for each group,
   wherein the processor is configured to:
   statistically analyze a predetermined medical image using a standardized image obtained by converting the predetermined medical image into the standard image or an inversely converted standard image obtained by inversely converting the standard image into the predetermined medical image, and
   calculate the standardized image or the inversely converted standard image by repeatedly performing conversion processing using the intermediate template according to the classification path stored in the storage unit.

7. The medical image processing apparatus according to claim 6,
   wherein the processor is configured to classify the predetermined medical image into any of the plurality of groups, and
   generate a standardized image of the predetermined medical image by repeating conversion image calculation using the intermediate template for the predetermined medical image according to the classification.

8. The medical image processing apparatus according to claim 6,
   wherein the processor is configured to classify the predetermined medical image into any one of the plurality of groups, and
   generate an inversely converted standard image by inversely converting the predetermined medical image by repeating conversion processing, which is opposite to the conversion when generating the standard image, on the standard image according to the classification.

9. The medical image processing apparatus according to claim 1,
   wherein the processor is configured to correct corrects the medical image before a repetitive operation.

10. The medical image processing apparatus according to claim 9,
    wherein the processor is configured to extract an abnormal region of the medical image, and
    correct the medical image by replacing extracted pixels of the abnormal region with pixel values of pixels in a surrounding region.

11. The medical image processing apparatus according to claim 9,
    wherein the processor is configured to correct the medical image before the classification of the medical image.

12. The medical image processing apparatus according to claim 9,
wherein the processor is configured to correct the medical image after the classification of the medical image, and
re-classify a medical image after being corrected.

13. A medical image analysis apparatus, comprising:
a processor coupled to a memory, the memory storing instructions that when executed by the processor, configure the processor to:
generate a standard image used for analysis of a medical image,
perform a statistical analysis using a standardized image obtained by converting the medical image into the standard image or an inversely converted standard image obtained by inversely converting the standard image into the medical image,
classify a plurality of medical images into a plurality of groups, calculate an intermediate template for each group, and
calculate a conversion image by performing conversion processing on an image forming each of the plurality of groups, the conversion processing being for conversion into an intermediate template for each group, and
the calculation of an intermediate template for each group and the calculation of a conversion image are repeated for the conversion image while reducing the number of groups, and the intermediate template for the group is set as the standard image when the number of groups becomes a minimum.

14. The medical image analysis apparatus according to claim 13, further comprising:
a display coupled to the processor,
wherein the processor is configured to receive a user designation regarding whether the analysis is an analysis using the standardized image or an analysis using the inversely converted standard image.

15. A non-transitory computer readable memory storing a standard image generation program for generating a standard image using a large number of medical images, the program causing a computer to execute:
a step of classifying the large number of medical images into a plurality of groups;
a step of calculating an intermediate template for each group;
a step of calculating a conversion image by performing conversion processing on an image forming each of the plurality of groups, the conversion processing being for conversion into an intermediate template for each group;
a step of repeating the calculation of an intermediate template for each group and the calculation of a conversion image, for the conversion image, while reducing the number of groups; and
a step of setting the template calculated in the template calculation step for the group as a template of the standard image when the number of groups becomes a minimum.

* * * * *